(12) United States Patent
Carpenter et al.

(10) Patent No.: US 8,616,785 B2
(45) Date of Patent: Dec. 31, 2013

(54) FIBER OPTIC COUPLER

(75) Inventors: Scott Carpenter, Elgin, IL (US); Tom Papanek, Lake Forest, IL (US)

(73) Assignee: Excelitas Technologies Corp., Waltham, MA (US)

( * ) Notice: Subject to any disclaimer, the term of this patent is extended or adjusted under 35 U.S.C. 154(b) by 296 days.

(21) Appl. No.: 12/705,392

(22) Filed: Feb. 12, 2010

(65) Prior Publication Data

US 2010/0209046 A1 Aug. 19, 2010

Related U.S. Application Data

(60) Provisional application No. 61/152,414, filed on Feb. 13, 2009.

(51) Int. Cl.
*G02B 6/36* (2006.01)

(52) U.S. Cl.
USPC .............................................. 385/89; 385/78

(58) Field of Classification Search
None
See application file for complete search history.

(56) References Cited

U.S. PATENT DOCUMENTS

| | | | |
|---|---|---|---|
| 5,396,572 A * | 3/1995 | Bradley et al. | 385/78 |
| 5,882,102 A | 3/1999 | Pileski | |
| 6,179,482 B1 * | 1/2001 | Takizawa et al. | 385/81 |
| 6,409,391 B1 | 6/2002 | Chang | |
| 6,848,836 B2 * | 2/2005 | Ueda et al. | 385/78 |
| 7,134,795 B1 * | 11/2006 | Bonna et al. | 385/82 |
| 7,226,215 B2 * | 6/2007 | Bareel et al. | 385/84 |
| 2004/0223702 A1 * | 11/2004 | Mine et al. | 385/78 |

\* cited by examiner

*Primary Examiner* — Tina Wong
(74) *Attorney, Agent, or Firm* — Peter A. Nieves; Sheehan Phinney Bass + Green, PA

(57) ABSTRACT

A coupler for coupling a light source to a fiber optic, comprising an adapter having a cavity for receiving the fiber optic, said adapter including pins extending in a direction perpendicular to the fiber optic's axis; a coupler body having an aperture for receiving the adapter, said aperture including a pair of through slots for receiving the pins, said body including interior pin sockets radially offset from the slots; a plate mounted within the coupler body; and biasing means urging said plate towards the aperture in the coupling body wherein when the adapter is inserted into the aperture of the coupler body, the adapter initially urges the plate in a direction away from the aperture, whereupon the adapter is rotated until the pins become aligned with and captured within the pin sockets allowing the plate to be urged in a direction back towards the aperture locking the coupler in place.

14 Claims, 8 Drawing Sheets

# FIBER OPTIC COUPLER

CROSS REFERENCE TO RELATED APPLICATION

This application claims priority to U.S. Provisional Application No. 61/152,414, filed Feb. 13, 2009, the disclosure of which is herein incorporated by reference in its entirety for all purposes.

BACKGROUND

1. Field

The present invention relates generally to fiber optics, and more particularly to devices for attaching a fiber-optic bundle to a light source.

2. Related Art

Systems comprising a light source and one or more fiber-optic bundles are used in a broad range of applications. In the medical field, fiber-optic illuminators are widely used in endoscopy and comprise various light sources, fiber-optics, and endoscopes; fiber-optic light systems providing "blue" light in the 420-490 nm wavelength range are used in photodynamic therapy for pediatric hyperbilirubinemia. Fiber-optic illumination systems are also used in industrial boroscopes and machine vision systems. Systems having light sources and fiber-optics for light transmission can also provide one or more defined wavelengths of light for fluorescent excitation in biological and other fields of research. In general illumination, light sources may distribute light over multiple fiber optics for spot or decorative lighting.

SUMMARY

Disclosed is an adapter specific to a particular fiber optic which is secured to the fiber optic light source by a user. Adaptors can be readily developed and manufactured for fiber optic configurations within a broad range of diameters and lengths. The dimensions of the holes in the adaptors ensure that the fiber optic is correctly positioned within the adapter and that the proper adapter is used with each fiber optic.

"Bayonet" features on the adaptor and light source coupler allow a user to insert the adaptor into the light source coupler by a simple push and turn motion. The fiber optic and adapter are easily removed from the light source coupler with a similar push and turn motion.

A spring-loaded plate within the light source coupler securely holds the adapter in its installed position and also ensures the desired relationship between the fiber optic and the internal optical components of the light source.

Other objects and advantages will become apparent hereinafter in view of the specification and drawings.

BRIEF DESCRIPTION OF THE FIGURES

The present application can be best understood by reference to the following description taken in conjunction with the accompanying drawing figures, in which like parts may be referred to by like numerals.

DETAILED DESCRIPTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems or methods of the present disclosure.

Figure 1:
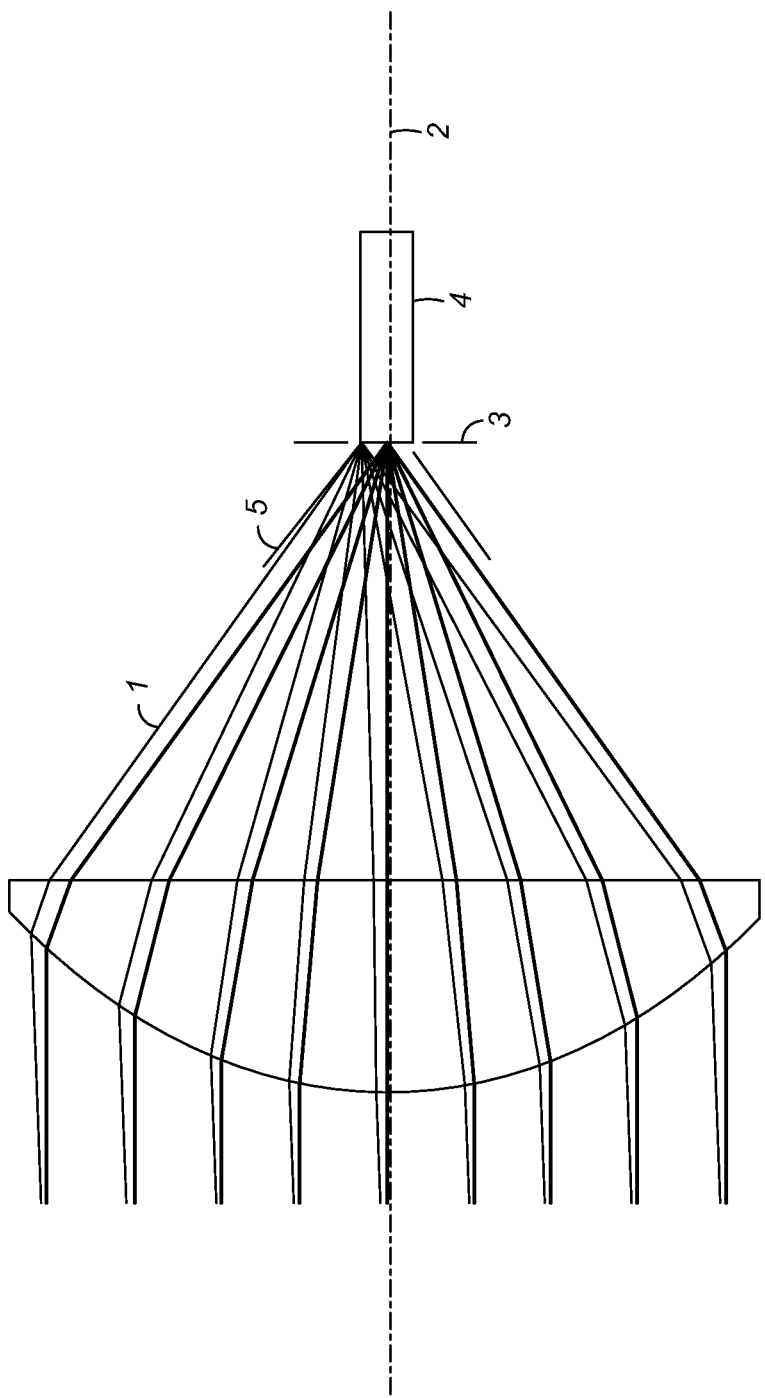
FIG. 1 illustrates a light source focusing light towards the input face of a fiber optic bundle.

Disclosed is a coupler that may be generally mounted to, or integrated with, the front outer housing (not shown) of a light source in which light is directed toward the input face of the fiber optic 4 as shown in FIG. 1. The light source may focus the light in a generally conical pattern 1 centered on optical axis 2 and focused at focal plane 3. The light enters fiber optic 4 having a light acceptance angle (numerical aperture NA) 5. Thus, it is desirable for the fiber optic 4 to be located co-axial with optical axis 2. It is also desirable for the input face of the fiber optic to be located co-planar with the optical focal plane 3.

Figure 2:
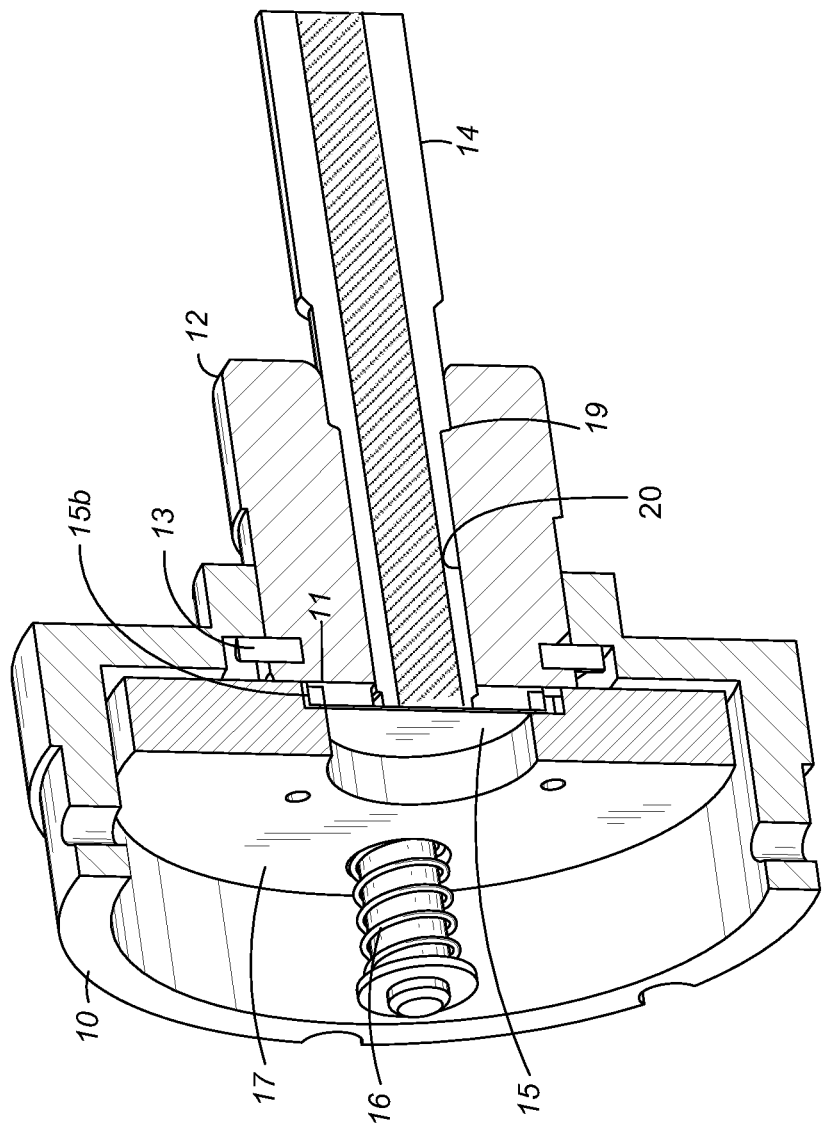
FIG. 2 illustrates a cross-sectional isometric view of an exemplary embodiment in accordance with the present application.

FIGS. 2-5 illustrate an exemplary embodiment in accordance with the present application. As shown in FIG. 2, the input end portion of a fiber optic bundle 14 can be inserted into the adapter 12 and secured within the adapter 12 by a binding screw or other means not shown. The adapter 12 has a cavity 20 to match the particular fiber optic. For example, the cavity 20 in adapter 12 may comprise two or more coaxial and contiguous cylindrical sections of diameters and depths appropriate to match the particular fiber optic. In this illustration, the adapter 12 has two such diameters. Because the adapter 12 has at least two internal diameters matched to the particular fiber bundle, a different fiber bundle will either not physically fit into the adapter 12 or the mismatch will be readily apparent to the user. Further, there will always be at least one "shoulder" 19 at the transition from one diameter to another, and adapters 12 are designed so that at least one shoulder serves as a fiber optic to adaptor interface positioning feature, to precisely position the input face 18 of the fiber optic 14 relative to the front face 11 of the adapter 12.

Since the adapter 12 is low-cost and can be easily removed from the light source coupler, the adapter 12 can remain on the fiber optic bundle 14 indefinitely or even be integrated into the design of the fiber optic bundle 14.

Figure 4:
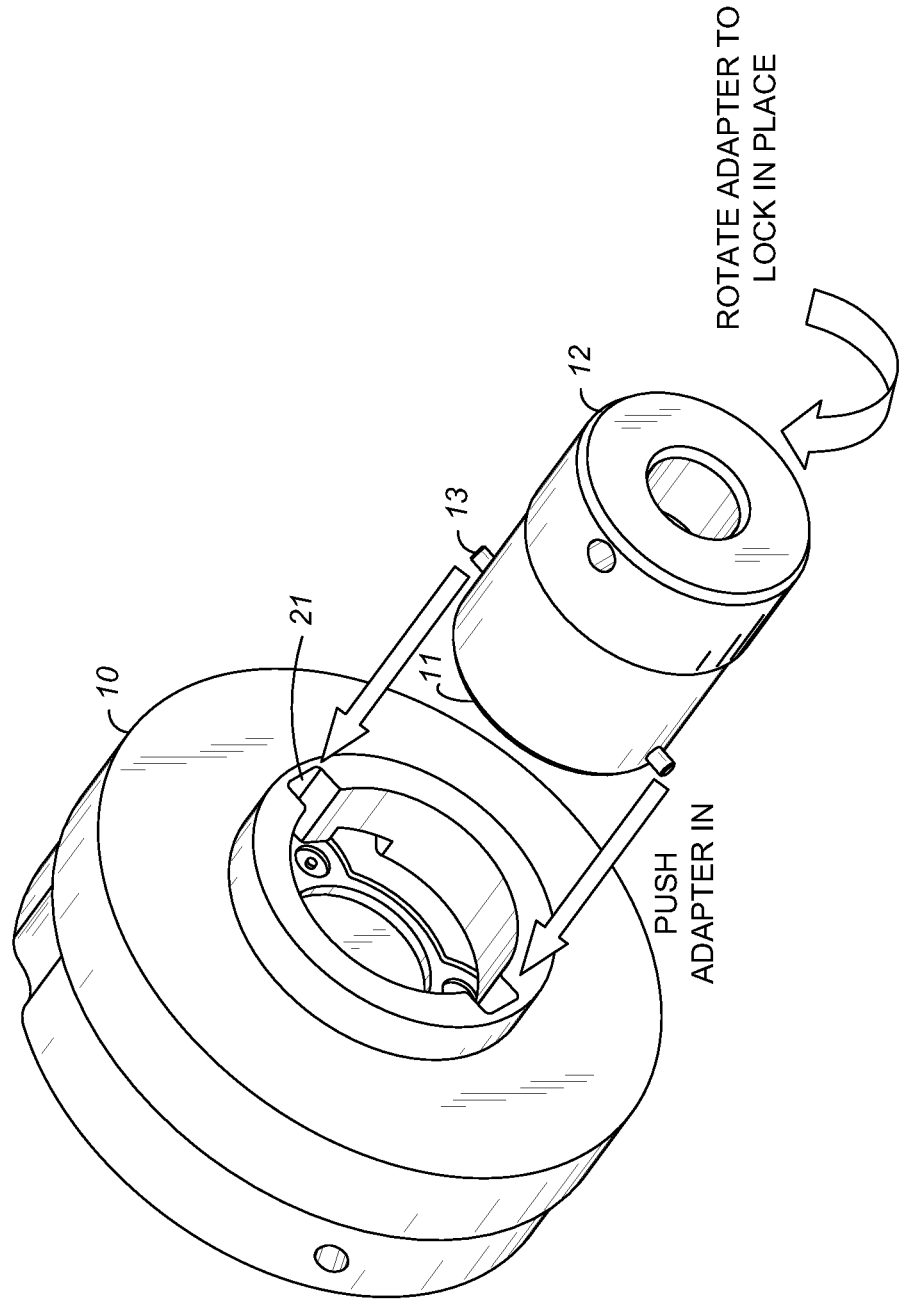
FIG. 4 illustrates the "bayonet" design of the exemplary embodiment shown in FIG. 2.
Figure 5:
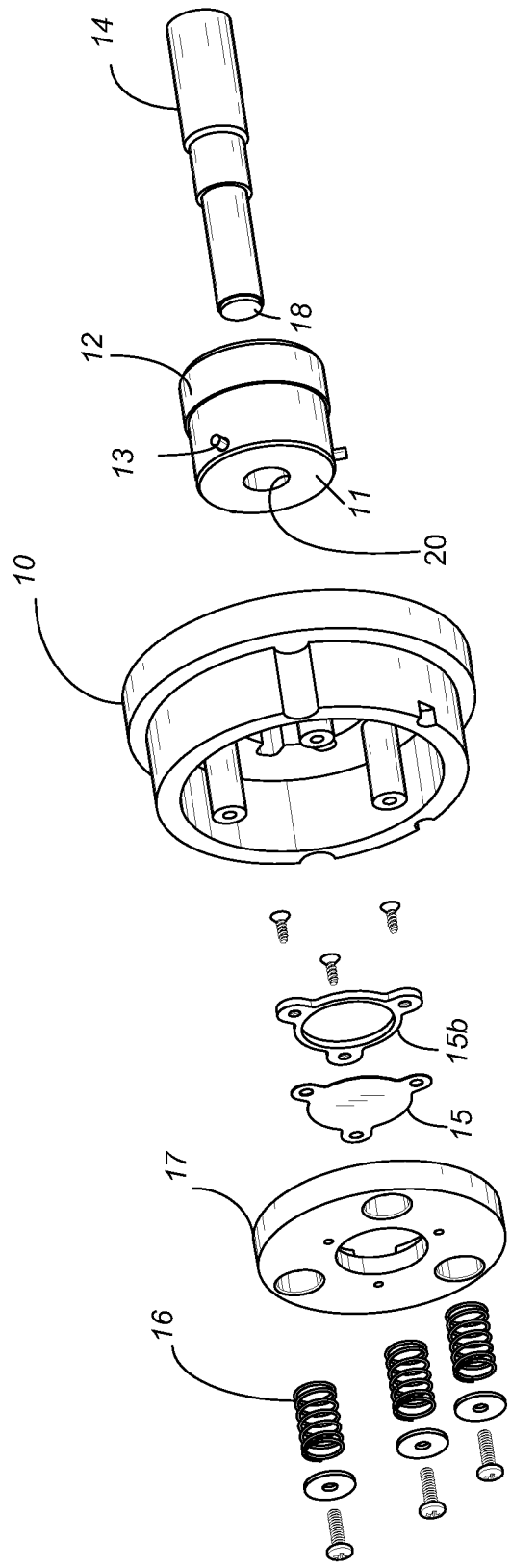
FIG. 5 illustrates an exploded view of the components in the exemplary embodiment shown in FIG. 2.

As shown in FIG. 4, the user may insert the adapter 12 into the coupler body 10 so that the bayonet pins 13 align with and enter into the coupler body bayonet slots 21. During this insertion, the front face 11 of the adapter 12 will contact and push against the moving plate 17. The moving plate 17 pushes against the adapter 12 due to the force applied by one or more springs 16. The springs 16 are chosen such that this outward force is sufficient to hold the adapter 12 in place once inserted, yet allows for easy insertion. For example, the total spring force may be in the range of approximately 0.2 to 2.2 lb (approximately 0.1 to 1.0 kg). As with other bayonet type fittings, the user may then rotate the adapter 12 through an angle of approximately 15° to 90° so that the bayonet pins 13 engage bayonet cams 22 in the coupler body 10.

Figure 3:
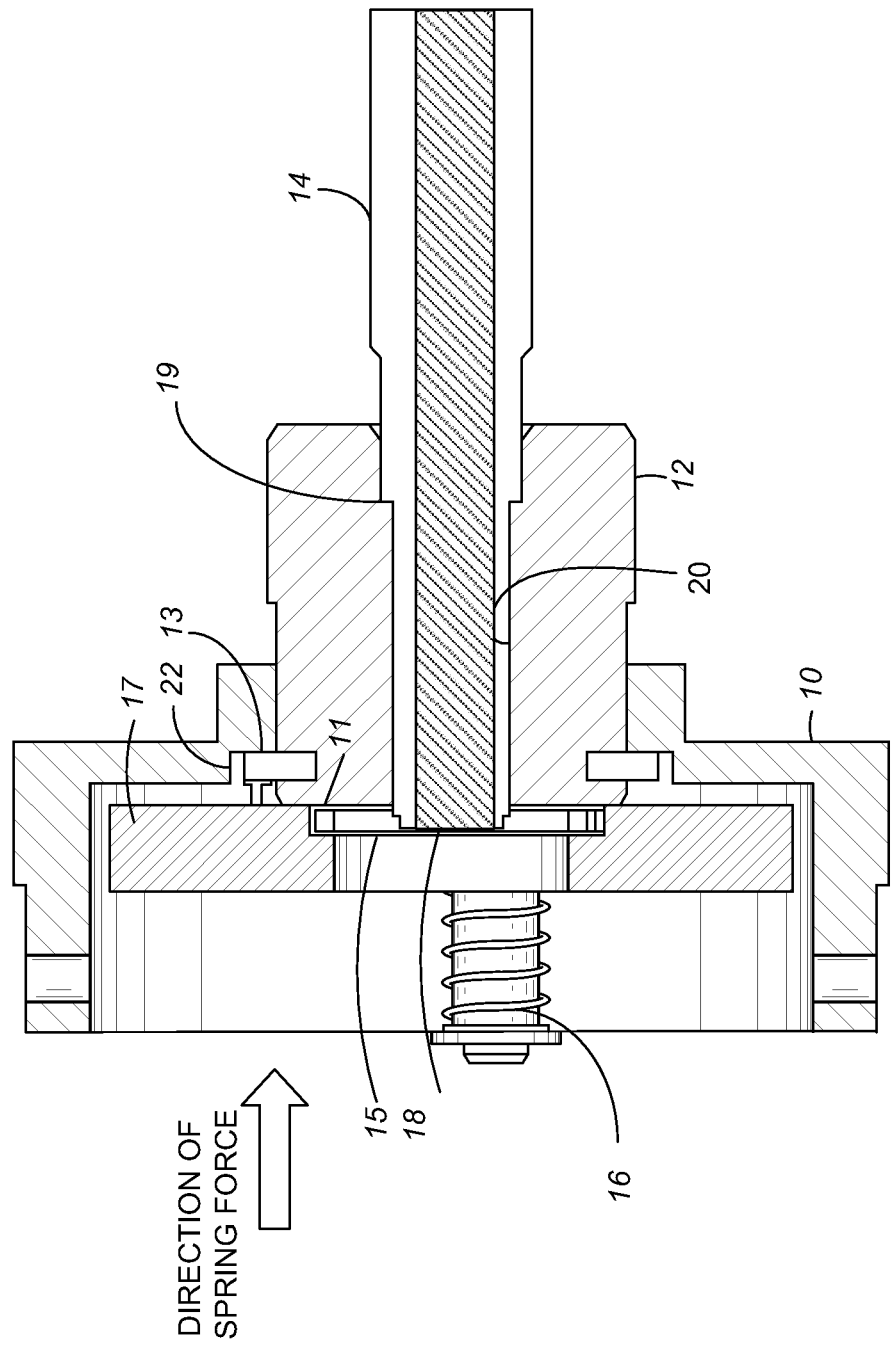
FIG. 3 illustrates the cross-sectional view of the exemplary embodiment shown in FIG. 2.

Because the moving plate 17 can move in a direction parallel to the axis of the adaptor 12 and is spring loaded as shown in FIGS. 2 and 3, any optical element 15 held in the moving plate 17 may be located with little or no gap against the input face 18 of the fiber optic 14. For example, the optical element 15 may be a holographic diffuser film affixed to moving plate 17 by clamping ring 15b. It is optically advantageous for the face of the optical element 15 to be parallel and held with little or no gap relative to the input face 18 of the fiber optic 14. This gap may be readily controlled because the front face 11 of adapter 12 presses against moving plate 17 and the input face 18 of the fiber optic 14 is located relative to the front face 11 of adapter 12 by adapter shoulder 19.

Figure 6:
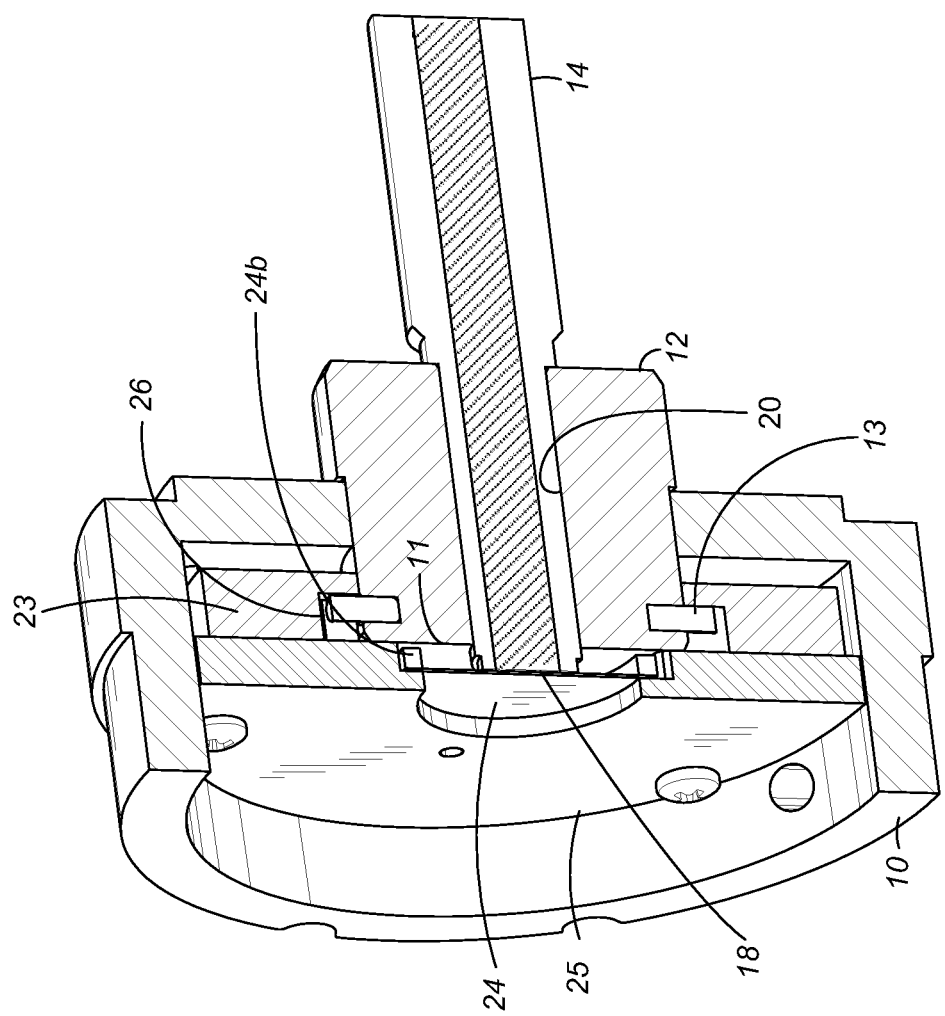
FIG. 6 illustrates a cross-sectional isometric view of a second exemplary embodiment in accordance with the present application.
Figure 7:
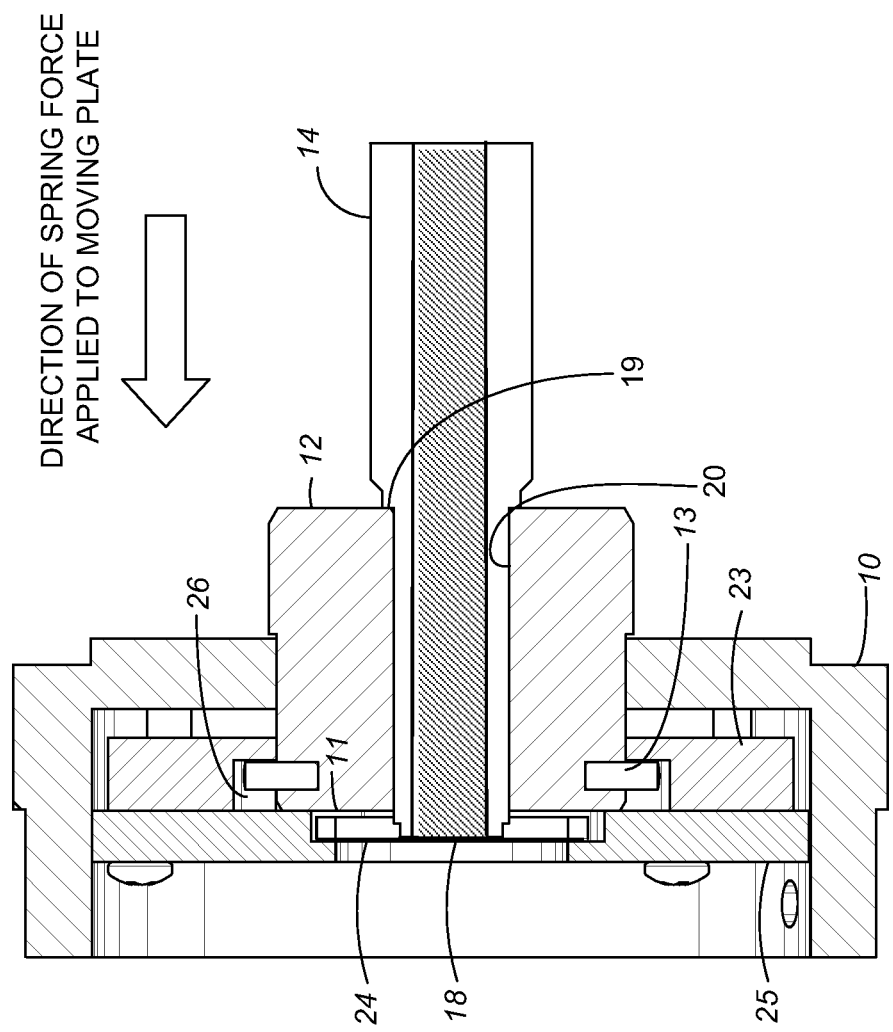
FIG. 7 illustrates the cross-sectional view of the exemplary embodiment shown in FIG. 6.
Figure 8:
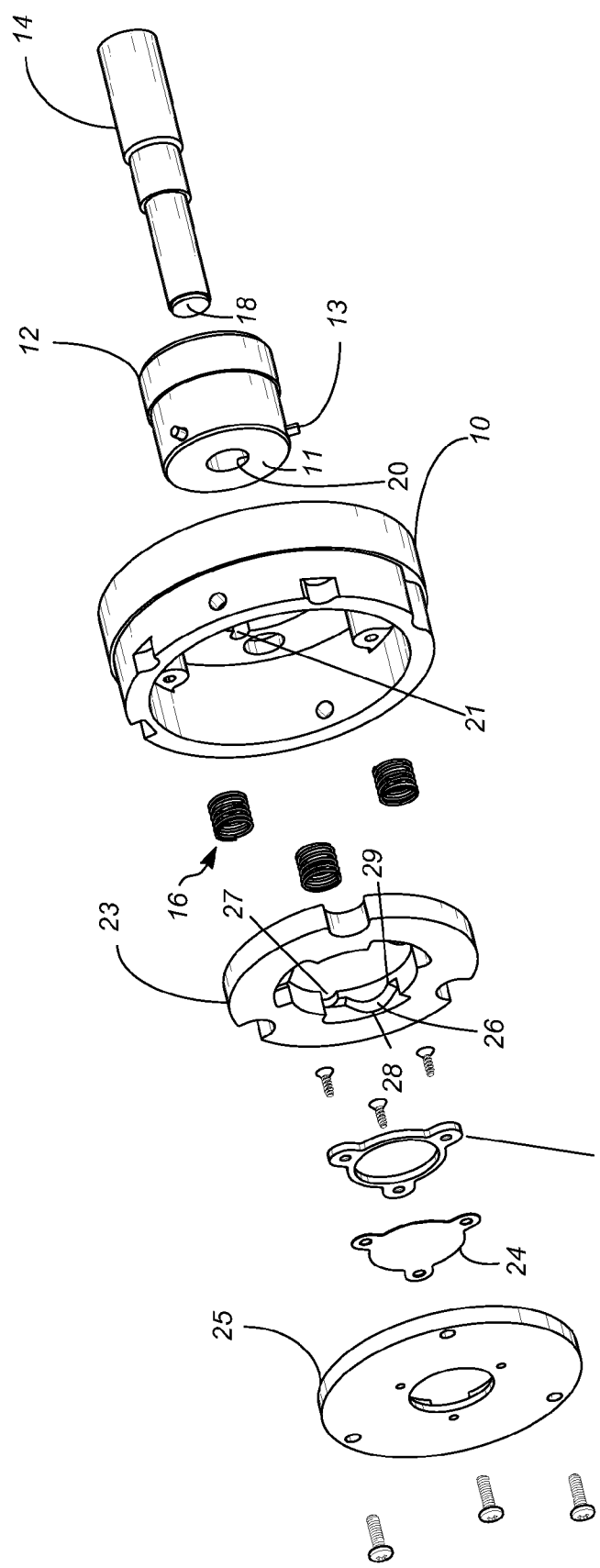
FIG. 8 illustrates an exploded view of the components in the exemplary embodiment shown in FIG. 6.

FIGS. 6-8 illustrate a second exemplary embodiment in accordance with the present application. The configuration and function of some components in the second exemplary embodiment are similar to the aforementioned embodiment; accordingly, only the distinct features are described below.

In the second exemplary embodiment, the moving plate 23, springs 16, and the additional fixed plate 25 are configured such that the moving plate 23 serves to pull the adapter 12 inward, as distinguished from the first exemplary embodiment, wherein the moving plate 17 exerts an outward force on the adapter 12.

Further, the bayonet cams 26 are located in the moving plate 23 in the second exemplary embodiment, rather than in the coupler body 10.

With reference to FIG. 8, in order to attach the adapter 12 into the coupler body 10, the bayonet pins 13 are aligned with the coupler body bayonet slots 21 on the coupler body 10 and the moving plate bayonet slots 27 on the moving plate 23. The bayonet pins 13 enter into the coupler body bayonet slots 21 and then further enter into the moving plate bayonet slots 27. Once the bayonet pins 13 reach the ends of the moving plate bayonet slots 27, the user may rotate the adapter 12 through an angle of approximately 15° to 90° so that the bayonet pins 13 engage bayonet cams 26 in the moving plate 23. Note that the bayonet cams 26 have an arc shape. As the bayonet pins 13 travel from the moving plate bayonet slots 27 to the top of the arc 28, the moving plate 23 is pushed towards the coupler body 10 and the adapter 12 (i.e., towards the right in FIG. 8). As the bayonet pins 13 travel to the end of the arc 29, the moving plate 23 is pushed away from the coupler body 10 and the adapter 12 (i.e., towards the left in FIG. 8). The springs 16 push against the moving plate 23 (i.e., towards the left in FIG. 8) and pull the adapter 12 inwards. When the adapter 12 has been fully inserted within the coupler body 10, the adapter face 11 will be in contact with fixed plate 25. Since the fiber optic face 18 is positioned relative to adapter face 11 by shoulder 19, the position of fiber optic face 11 will be precisely located with respect to fixed plate 25.

In the second exemplary embodiment, an optical element such as a holographic diffuser 24 is mounted by a clamp ring 24b within the fixed plate 25, which in turn is fixed within the coupler body 10. Since the position of fiber optic face 18 will be precisely located with respect to fixed plate 25, the gap between fiber optic face 16 and optical element 24 will be equally controlled, which prevents damage to the optical element and is optically advantageous.

To the extent that the coupler body 10 and the fixed plate 25 are located precisely with respect to the light source optics, the input face 18 of the fiber optic 14 will be precisely located at the focal plane of the light source, which is optically advantageous. Further, the spring force acting in concert with the bayonet features will aid in angular alignment of the fiber optic 14 with respect to the optical center axis.

Other variations of the present designs may be made.

The methods and systems described herein are not limited to a particular hardware or software configuration, and may find applicability in many computing or processing environments. The methods and systems can be implemented in hardware or software, or a combination of hardware and software.

Unless otherwise stated, use of the word "substantially" can be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun can be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, can be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, can be made by those skilled in the art. Accordingly, it will be understood that the present disclosure is not to be limited to the embodiments disclosed herein, can include practices otherwise than specifically described, and is to be interpreted as broadly as allowed under the law.

What is claimed is:

1. A coupler for releasably coupling a light source to a single fiber optic bundle, comprising:

an adapter having a front face and a cavity for receiving the fiber optic bundle with an input face positioned relative to said front face, said adapter including at least two pins extending outwardly therefrom in a direction perpendicular to the axis of the fiber optic bundle;

a coupler body having a central aperture for receiving the adapter, said aperture including a pair of through slots for receiving the pins of the adapter, said body further including a pair of interior pin sockets radially offset from the slots;

a substantially flat plate mounted within the coupler body and having a central aperture aligned with the central aperture of the coupler body, the plate central aperture having a diameter less than the outer diameter of the adapter; and biasing means urging said plate towards the aperture in the coupling body wherein when the adapter is inserted into the aperture of the coupler body, the adapter initially urges the plate in a direction away from the aperture, whereupon the adapter is rotated until the pins become aligned with and captured within the pin sockets allowing the plate to be urged in a direction back towards the aperture locking the coupler in place, wherein said received adapter front face presses against the plate so an interface between said input face and the light source is positioned substantially within said coupler body.

2. The coupler of claim 1, wherein the central aperture in the plate is covered by an optical element.

3. The coupler of claim 2, wherein the optical element is a holographic diffuser film.

4. The coupler of claim 1 wherein the central aperture in the plate is covered by a transparent stop plate.

5. The coupler of claim 1, wherein the cavity in the adapter is dimensioned to match the dimensions of the portion of the fiber optic bundle received by the adapter.

6. The coupler of claim 5, the cavity comprising two coaxial and contiguous cylindrical sections, the two cylindrical sections having different diameters, and wherein the shoulder in the adapter at the transition from the first diameter to the second diameter sets the position of the input face of the fiber optic bundle relative to the front face of the adapter.

7. The coupler of claim 1, wherein as received by the coupler body, the adapter positions the fiber optic bundle in a co-axial orientation with respect to an optical axis of the light source, and positions the input face of the fiber optic bundle co-planar with an optical focal plane of the light source.

8. A coupler for releasably coupling a light source to a fiber optic bundle, comprising:

an adapter having a cavity for receiving the fiber optic bundle, said adapter including at least two pins extending outwardly therefrom in a direction perpendicular to the axis of the fiber optic bundle;

a coupler body having a central aperture for receiving the adapter, said aperture including a pair of through slots for receiving the pins of the adapter;

a fixed plate mounted within the coupler body and spaced from the central aperture of the coupler body, said fixed plate having a central aperture;

a movable plate mounted within the coupler body between the fixed plate and the aperture, said movable plate having a central aperture aligned with the central aperture of the coupler body, said movable plate including a pair of through slots for receiving the pins of the adapter and a pair of interior pin sockets radially offset from the slots and located on the surface of the movable plate facing the fixed plate; and biasing means urging said movable plate towards the fixed plate wherein during the connection of the adapter to the coupler, the adapter is initially inserted into the aperture of the coupler body with the pins passing through the through slots in the coupler body and the through slots of the movable plate, wherein the adapter is configured to be rotated causing the movable plate to be urged towards the aperture in the body until the pins become captured within the pin sockets allowing the movable plate to be urged in a direction back towards the fixed plate locking the coupler in place.

9. The coupler of claim 8, wherein the movable plate includes a cam surface between the through slots and the pin sockets for guiding the pins during rotation of the adapter.

10. The coupler of claim 8, wherein the central aperture in the fixed plate is covered by an optical element.

11. The coupler of claim 10, wherein the optical element is a holographic diffuser film.

12. The coupler of claim 8, wherein the central aperture in the fixed plate is covered by a transparent stop plate.

13. The coupler of claim 8, wherein the cavity in the adapter is dimensioned to match the dimensions of the portion of the fiber optic bundle received by the adapter.

14. The coupler of claim 13, the cavity comprising two coaxial and contiguous cylindrical sections, the two cylindrical sections having different diameters, and wherein the shoulder in the adapter at the transition from the first diameter to the second diameter sets the position of the input face of the fiber optic bundle relative to the front face of the adapter.

* * * * *